United States Patent
Agterberg et al.

(10) Patent No.: US 6,392,037 B1
(45) Date of Patent: May 21, 2002

(54) PROCESS FOR THE PREPARATION OF ε-CAPROLACTAM

(75) Inventors: Frank P. W. Agterberg, Nieuwstadt; Nicolaas F. Haasen, Sittard; Rudolf P. M. Guit, Maastricht, all of (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 09/925,730

(22) Filed: Aug. 10, 2001

Related U.S. Application Data

(63) Continuation of application No. PCT/NL00/00068, filed on Feb. 3, 2000.

(30) Foreign Application Priority Data

Feb. 12, 1999 (EP) .............................................. 99200411

(51) Int. Cl.[7] ............................................ C07D 201/08
(52) U.S. Cl. ...................................................... 540/538
(58) Field of Search ........................................ 540/538

(56) References Cited

U.S. PATENT DOCUMENTS

| 3,658,810 A | 4/1972 | Tanaka et al. ........... 260/239.3 |
| 5,693,793 A | 12/1997 | Ritz et al. ................... 540/539 |

FOREIGN PATENT DOCUMENTS

| EP | 0340827 | 11/1989 |
| EP | 0826666 | 3/1998 |
| WO | 9837063 | 8/1998 |
| WO | 9852904 | 11/1998 |

*Primary Examiner*—Bruck Kifle
(74) *Attorney, Agent, or Firm*—Pillsbury Winthrop LLP

(57) ABSTRACT

Process for the preparation of ε-caprolactam comprising treating 6-aminocaproic acid 6-aminocaproate ester, 6-aminocaproamide, oligomers or polymers of these compounds or mixtures comprising at least two of these compounds in a cyclisation reactor in the presence of superheated steam in which a gaseous product stream comprising ε-caprolactam, lights and heavies is obtained, wherein the product stream, after condensation and at least partial removal of water and lights, is split into a ε-caprolactam stream and a heavies stream containing heavies and ε-caprolactam and the heavies stream is recycled to a cyclisation reactor.

9 Claims, No Drawings

PROCESS FOR THE PREPARATION OF ε-CAPROLACTAM

CROSS-REFERENCE TO RELATED APPLICATIONS

This Application is a continuation of International Application PCT/NL00/00068, filed Feb. 3, 2000, which designated the U.S. and was published in the English language.

The invention relates to a process for the preparation of ε-caprolactam comprising treating 6-aminocaproic acid, 6-aminocaproate ester, 6-amino-caproamide, oligomers or polymers of these compounds or mixtures comprising at least two of these compounds in a cyclisation reactor in the presence of superheated steam in which a gaseous product stream comprising ε-caprolactam, steam, lights and heavies is obtained.

Compounds having a higher boiling point than ε-caprolactam are designated as heavies in this specification. Examples are 6-aminocaproic acid, 6-aminocaproamide, oligomers of these compounds, ε-caprolactam cyclic oligomers N-substituted or C-substituted lactams and/or amides. Compounds having a lower boiling point than ε-caprolactam are designated as lights in this specification. Examples are N-methyl-ε-caprolactam, hexanoic acid, 5-hexenoic acid, valeric acid and valeramide.

Such a process is described in WO-A-9837063. This patent publication describes a process to prepare ε-caprolactam by treating 6-aminocaproic acid, 6-aminocaproate ester and/or 6-aminocaproamide with superheated steam at a temperature of between 250–400° C. and a pressure of between 0.5 and 2 MPa. The crude ε-caprolactam obtained still contains impurities and requires further purification. The crude ε-caprolactam product stream obtained in the cyclisation process as described in WO-A-9837063 also contains lights and heavies. The majority of these lights and heavies need first to be removed in order to make efficient purification of ε-caprolactam possible in the subsequent purification steps. Lights and heavies are usually separated from the ε-caprolactam product stream with distillation. A disadvantage of the separation of the heavies from the ε-caprolactam product stream is that it is almost impossible or very difficult to quantitatively separate ε-caprolactam from the heavies without degradation of ε-caprolactam and/or fouling of the separation equipment. Another disadvantage is that the valuable ε-caprolactam precursors are not recovered. For a commercially interesting process it is advantageous to recover the greatest part of ε-caprolactam and ε-caprolactam precursors from the heavies before the heavies are disposed off.

An object of the invention is to provide a simplified process for the preparation of ε-caprolactam. Still another object is to get a high yield of ε-caprolactam.

These objects are achieved in that the product stream, after condensation and at least partial removal of water and lights is split into a ε-caprolactam stream and a heavies stream containing heavies and ε-caprolactam and the heavies stream is recycled to a cyclisation reactor.

It has been found that with the process according to the invention high yields to ε-caprolactam can be achieved. Another advantage is that the separation of ε-caprolactam from the heavies does not need to be quantitatively. In the process according to the invention the distillative separation of ε-caprolactam and heavies can be performed at a less reduced pressure and/or temperature compared to a process in which there is no recycle of the heavies stream for obtaining comparable yields of ε-caprolactam.

Preferably the heavies stream is recycled to the cyclisation reactor from which the product stream is derived. This is advantageous from an economical/investment point of view because no additional cyclisation reactor is needed.

Before recycling the heavies stream to the cyclisation reactor, the heavies stream is optionally first fed to another separation unit in which the heavies stream is further split into a ε-caprolactam stream and a second heavies stream. This second heavies stream is subsequently recycled to the cyclisation reaction. Examples of possible separation units are extractors and stripper columns. A preferred separation unit is a stripper column. More preferably a gaseous stream containing steam is fed to the stripper column to strip ε-caprolactam from the heavies stream resulting in a gaseous ε-caprolactam containing top stream. The gaseous ε-caprolactam containing top stream can easily be integrated in the purification section (described below) of the product stream from the cyclisation reactor.

With a cyclisation reactor is meant a reactor in which an open-chain compound is converted into a compound that contains a ring, a process called cyclisation. In the process according to the invention 6-aminocaproic acid, 6-aminocaproate ester and/or 6-aminocaproamide is cyclised into ε-caprolactam.

The process according to the invention can be performed in a reactor which is provided with an inlet for the starting compound(s), an outlet for the steam/ε-caprolactam product and means for supplying steam such that the steam is contacted with the starting material. The reactor is optionally equiped with a heating device and optionally with a mixing device. To this reactor the starting compound and the steam can be continuously fed. A possible reactor is a fluidized bed reactor containing inert particles in which the bed is kept fluidized by the steam. Another example of a reactor is a horizontal tube reactor having a rotating axis on which axis means for mixing and/or transport are present. Also means are possible present which prevent fouling of the interior vessel wall and which promote an optimal steam/substrate contact area for mass-transfer.

Examples of suitable cyclisation reactors are a packed tower-type reactor, one or multiple staged bubble columns or a multi-tube reactor. In case the cyclisation reactor consists of two or more reactor vessels in series, the heavies stream or bottom stream from the stripper is preferably fed to the last reactor vessel.

A possible process according to the invention is schematically represented in FIG. 1.

In the cyclisation reactor (1) the gaseous stream (1a) comprising ε-caprolactam, steam, lights and heavies is obtained.

The starting mixtures comprising 6-aminocaproic acid, 6-aminocaproate ester, 6-aminocaproamide, oligomers of these compounds and/or polymers of these compounds can be obtained by various processes. For example in U.S. Pat. No. 4730040 a process is described in which an aqueous mixture is obtained containing 6-aminocaproic acid and some ε-caprolactam starting from 5-formylvalerate ester. Further in EP-A-729943 a process is described in which an aqueous mixture is obtained containing 6-aminocaproic acid, 6-aminocaproamide and ε-caprolactam also starting from a U.S. Pat. No. 5-formylvalerate ester. US-A-5068398 describes a process in which an aqueous mixture is obtained containing 6-aminocaproate ester and some ε-caprolactam starting from a 5-formylvalerate ester.

Other examples of starting mixtures which can be used in the process according to the invention are polycaprolactam processing waste, polycaprolactam carpet waste and/or polycaprolactam extraction wash water.

The starting compound or mixture of starting compounds which are obtainable by the above described processes, are preferably contacted with the superheated steam as a liquid, for example as a melt.

Polycaprolactam waste is preferably fed to the reactor as a melt. This feeding may be achieved by using an extruder, gear pump, or other means known in the art.

Starting mixtures can also be obtained starting from 6-aminocapronitrile as for example described in WO-A-9837063.

The cyclisation is preferably performed as described in WO-A-9837063.

The condensation and at least partial removal of water, lights and heavies from the product stream can be conducted in the following steps:

a) the product stream is fed to a partial condensation unit (2), and split in a top stream comprising steam (2t) and a liquid bottom stream
(2b) comprising ϵ-caprolactam, water, lights and heavies;

b) the bottom stream (2b) is fed to a distillation column (3) of which the top stream (3t) is mainly water and the bottom stream (3b) comprises ϵ-caprolactam, lights and heavies;

c) the bottom stream (3b) is fed to a vacuum distillation column (4) of which the top stream (4t) is mainly lights and the bottom stream (4b) comprises ϵ-caprolactam and heavies;

d) the bottom stream (4b) is fed to a vacuum distillation column (5) of which the top stream (5t) is the ϵ-caprolactam stream and the bottom stream (5b) is the heavies stream.

The condensation of the product stream (step a)) is preferably performed at a temperature of 80–200° C., more preferably at a temperature of 100–170° C.

The distillation in step b) is for example performed at a temperature of 60–160° C., preferably at a temperature of 80–140° C.

The distillation in step c) and d) is preferably performed at a pressure lower than 10 kPa, more preferably at a pressure lower than 5 kPa. The temperature of the distillation in step c) and d) is preferably between 110°–170° C., more preferably between 120–150° C.

Preferably a part of the residue in the cyclisation reactor and/or a part of the heavies stream (5b) is purged (stream (5c)) and the rest is recycled to a cyclisation reactor, preferably to the cyclisation reactor from which the product stream is derived.

The ϵ-caprolactam streams resulting from the process according to the invention can be purified according to conventional techniques. Advantageously the caprolactam is purified by a crystallisation process.

The purification of ϵ-caprolactam by crystallisation can be conducted in the following steps:

e) the ϵ-caprolactam stream (5t) is fed as a liquid ϵ-caprolactam stream into a crystallizer (6), in which conditions are set such that ϵ-caprolactam crystals and a mother liquid are formed (stream (6a)), f) the stream (6a) from the crystallizer is fed to a separator (7), and split to purified ϵ-caprolactam (7a) and a mother liquid (7b), g) the mother liquid (7b) is recycled to the crystallizer (6).

Preferably, a part of the mother liquid (7b) is purged and the purge is recycled to the distillation column (3) or to the distillation column (4).

The crystallizer (6) is operated such that crystallization of ϵ-caprolactam occurs through cooling. In the crystallizer (6) relatively pure ϵ-caprolactam crystals are formed (solid phase) and a mother liquid, which comprises ϵ-caprolactam, impurities and optionally solvent (liquid or melt phase). The solid phase in the crystallizer can have a different appearance, depending on the way the crystallization is performed. The crystallization in the crystallizer (6) can be performed for example either by cooling via a heat exchanging surface (suspension or layer crystallization) or by adiabatic cooling by evaporation of part of the contents of the crystallizer, for instance a solvent, under reduced pressure (crystallization in suspension). The method of crystallization induced by reduced pressure cooling is preferred, since no crystallization on inner surfaces of the crystallizer occurs. In reduced pressure cooling the condensed vapour from the crystallizer may or may not be returned, totally or partially to the contents of the crystallizer. Preferably the crystallizer is operated by evaporating the solvent under reduced pressure.

Preferably solvent is present in the mixture in the crystallizer, although crystallization can also be conducted without solvent. Many solvents are suitable. Examples of suitable solvents are water, alkanes (like n-hexane, n-heptane, iso-octane, cyclohexane), alcohols (like methanol, ethanol, n-propanol, butanol), aromatic hydrocarbons (like benzene, toluene, o-xylene, m-xylene, p-xylene), ammonia, chlorinated hydrocarbons (like tetrachloromethane, chloroform or ethylchloride), ketones like acetone or methylethyl keton) and esters (like ethyl acetate). Preferably water and aromatic hydrocarbons are used as solvent, since these solvents give large crystals. Most preferred as solvent is water. The solvent will act as a freezing point depressor for the melt in the crystallizer.

The concentration of solvent in the melt in the crystallizer is dependent on the solvent, the amounts of impurities in the feed ϵ-caprolactam and the way the cooling in the crystallizer is performed. With the preferred solvent water and reduced pressure cooling the concentration of water in the melt is usually below 20 weight %, preferably 1–15 weight % and more preferred 2–10 weight %.

A solvent stream may be directly fed to the crystallizer and/or is mixed with the liquid crude ϵ-caprolactam feed stream prior to being fed to the crystallizer.

The temperature of the mixture in the crystallizer is dependent on the presence and concentration of solvent and impurities in the mixture, but at most 69° C., being the melting temperature of pure ϵ-caprolactam. Preferably the temperature of mixture in the crystallizer is 20–69° C., more preferable 35–67° C. The crystallizer can be operated in batch or in continuous mode. Preferably the crystallizer is operated in a continuous mode.

The separator (7) may be any separator that is capable of separating crystals from the mother liquid, e.g. a filter working under forces like gravity, reduced pressure, increased pressure or a centrifuge. Various types of filters and centrifuges can be used. In these separators during or after separation washing of the crystals is possible and preferred. The separator (7) is for instance a horizontal vacuum belt filter. This type of solid-liquid separator has an excellent washing efficiency. Another example of a separator is a crystal washcolumn, in which the crystals are compacted into a packed bed which bed is transported with gravity, hydraulic pressure or a mechanical means. An example of a crystal washcolumn in which the crystal bed is transported with a mechanical means is a Niro screw-type wash column system as for example described in 'European Chemical News', Jun. 30–Jul. 6, 1997, page 23. A crystal washcolumn has the advantage that an effective separation of the ε-caprolactam crystals from the mother liquid is achieved and simultaneously very effective washing of the crystals is performed. A more preferred crystal washcolumn is the so-called TNO-Thijssen hydraulic wash column as described in "Improved procedures for separating crystals for the melt",D. Verdoes, G. J. Arkenbout et al., Applied Thermal Engineering, 17 (8–10), 1997, 879–888.

In the TNO-Thijssen hydraulic wash column, the purified ε-caprolactam crystals are removed from the crystal bed and subsequently molten by a heat exchanger. A part of the molten ε-caprolactam crystals is recycled to the crystal washcolumn as washing liquid. The ε-caprolactam washing liquid finally crystallizes on the surface of ε-caprolactam crystals present in the so-called washfront. This is advantageous because, with a minimum quantity of washing liquid, a very effective separation of the ε-caprolactam crystals from the mother liquid and simultaneously a high washing efficiency of the ε-caprolactam crystals is achieved. In the TNO-Thijssen hydraulic wash column the purified ε-caprolactam is obtained as a liquid melt (stream 7a).

Advantageously the purified ε-caprolactam (7a) from the separator (7) is further purified in a second crystallization step (crystallizer (8)) followed by a second separation/washing step (separator (9)) of the ε-caprolactam crystals. This second crystallization step may be performed in a similar way as the first crystallization step. The separation and effective washing of the ε-caprolactam crystals from the mother liquid can be performed in a solid-liquid separation equipment as described for separation/washing step (7). Preferably stream (8a) leaving from the second crystallizer (8) comprising ε-caprolactam crystals and a mother liquid, is fed to a second crystal wash column (9) and split to a mother liquid and purified ε-caprolactam. The mother liquid is recycled to crystallizer (8). Preferably a part of the mother liquid is recycled to the first crystallizer (6). If necessary additional crystallization steps and separation/washing steps are possible.

The invention will be elucidated by the following examples, however these are not intended to limit the scope of the invention in any way.

Example 1

A 500 ml autoclave having a turbine mixer was continuously fed with a concentrated organic substrate mixture of ε-caprolactam precursors and steam. The composition of the organic feed mixture was (wt %) 33.9% of ε-caprolactam, 10.9% of 6-aminocaproic acid, 38.3% of 6-aminocaproic amide, 13.6% of Nylon-6-oligomers and 3.3% of water. The autoclave was initially charged with 61 grams of the same organic feed mixture. After flushing with nitrogen and adjusting the pressure valve such that the pressure in the reactor was 1.2 MPa, the temperature was raised to 300° C. At the same time the continuous feed of the organic mixture was started at a rate of 38 g/hr and the steam feed at a rate of 222 g/hr. The ε-caprolactam content of the product phase was continuously analyzed. After approximately 10 hours a steady-state was reached at a ε-caprolactam concentration in the condensate of 12.9 wt %. The reactor contents at steady state amounted to approximately 100 grams, present as oligomers of ε-caprolactam and 6-aminocaproic acid. After 29 hours the feed rate was increased to 57 g/hr of the organic feed and 333 g/hr of steam. At that point of the continuous run the overall conversion of the ε-caprolactam precursors fed to the reactor was approximately 91%.

After another 10 hours, the ε-caprolactam concentration in the condensed steam was 12.9 wt % indicating that steady-state was reached again. The reactor contents in the new steady-state conditions was approximately 140 grams. The reaction was continued for a total of 54 hrs. The overall conversion of εe-caprolactam precursors fed in total was 94.4% at the end of the run. Subsequently the substrate feed was stopped and the run was continued in batch-mode at a steam-feed of 390 g/hr. After 7 hours the condensed steam contained approximately 120 gram of ε-caprolactam. The autoclave contained 7 grams of residue, corresponding to an overall conversion of 99.7% of the organic feed. Overall 17700 gram of an aqueous product mixture was obtained which contained approximately 12.9 wt % ε-caprolactam. Subsequently the excess of water was evaporated using a rotary evaporator at a pressure of 10.5 kPa and a water bath temperature of 60° C., yielding 3130 gram 72.8 wt % aqueous ε-caprolactam solution. The composition of this product was analyzed using HPLC and GC-MS methods. Excluding water, the product contained 98.0 wt % ε-caprolactam. Approximately 0.9 wt % of light impurities and 1.1 wt % of heavy impurities were present.

Subsequently residual water, lights and heavies were successively removed by batch distillation of the product in three separate distillation stages using a laboratory vigreux column. During the first stage mainly water was removed at a column pressure that was gradually reduced from 8 to 0.2 kPa and the bottom temperature increased from 62 to 85° C. In the second stage the lights fraction was distilled off at a column pressure of 0.3 kPa and a bottom temperature that gradually increased from 91 to 122° C. At the end of this stage approximately 3% of the ε-caprolactam was collected in the light fractions. In the third stage 2150 gram (95.1%) of the ε-caprolactam was distilled over the top at a pressure of 0.1 kPa and a bottom temperature gradually raising from 120 to 140° C. At the end of this stage 68 grams of residue was collected. According to the mass-balance 1.7% of the original amount of ε-caprolactam ended up in this heavies residue, corresponding to approximately 60% of the total weight of this residue fraction. Subsequently, the heavies residue was used as substrate in the following batch experiment:

A 500 ml autoclave having a turbine mixer was filled with the heavies residu. The autoclave was substantially flushed with nitrogen and a pressure valve was adjusted such that the pressure in the reactor was maintained at 1.2 MPa. When the temperature reached 300° C. a steam flow was started at a rate of 300 g/hr. The steam containing ε-caprolactam leaving the reactor was condensed and analyzed. After 5 hours the condensed steam contained approximately 62 grams of ε-caprolactam, which corresponds to a practically complete conversion of ε-caprolactam precursors to ε-caprolactam. The resulting approximately 2 grams of residue did not yield any more caprolactam upon extended reaction.

EXAMPLE II

Example I was repeated,except that the feed consisted of nylon-6 spin-chips. 100.1 grams of nylon-6 spin-chips (type GL 1030, size 2.0×3.0 mm (d×L)) was charged to the autoclave. The autoclave was subsequently flushed with nitrogen and a pressure valve was adjusted such that the pressure in the reactor was maintained at 1.2 MPa. When the temperature reached 300° C. a steam flow was started at a rate of 260 g/hr. The steam containing ε-caprolactam leaving the reactor was condensed and analyzed. After 5 hours the condensed steam contained a total of 98 g ε-caprolactam, corresponding to 98% yield. The autoclave was virtually empty on visual inspection.

What is claimed is:

1. Process for the preparation of $\epsilon$-caprolactam comprising treating 6-aminocaproic acid, 6-aminocaproate ester, 6-amninocaproamide, oligomers or polymers of these compounds or mixtures comprising at least two of these compounds in a cyclisation reactor in the presence of superheated steam in which a gaseous product stream comprising $\epsilon$-caprolactam, steam, lights and heavies is obtained, wherein the product stream, after condensation and at least partial removal of water and lights, is split into a $\epsilon$-caprolactam stream and a heavies stream containing heavies and $\epsilon$-caprolactam and the heavies stream is recycled to a cyclisation reactor.

2. Process according to claim 1, wherein the heavies stream is recycled to the cyclisation reactor from which the product stream is derived.

3. Process according to claim 1, wherein the condensation and the at least partial removal of water, lights and heavies from the product stream is conducted in the following steps:
   a) the product stream is fed to a partial condensation unit (2), and split in a top stream comprising steam (2t) and a liquid bottom stream (2b) comprising $\epsilon$-caprolactam, water, lights and heavies;
   b) the bottom stream (2b) is fed to a distillation column (3) of which the top stream (3t) is mainly water and the bottom stream (3b) comprises $\epsilon$-caprolactam, lights and heavies;
   c) the bottom stream (3b) is fed to a vacuum distillation column (4) of which the top stream (4t) is mainly lights and the bottom stream (4b) comprises $\epsilon$-caprolactam and heavies;
   d) the bottom stream (4b) is fed to a vacuum distillation column (5) of which the top stream (5t) is the $\epsilon$-caprolactam stream and the bottom stream (5b) is the heavies stream.

4. Process according to claim 1, wherein the $\epsilon$-caprolactam stream is purified using a crystallization process.

5. Process according to claim 4, wherein the purification of $\epsilon$-caprolactam is conducted in the following steps:
   e) the caprolactam stream (5t) is fed as a liquid $\epsilon$-caprolactam stream into a crystallizer (6), in which conditions are set such that $\epsilon$-caprolactam crystals and a mother liquid are formed (stream (6a)),
   f) the stream (6a) from the crystallizer is fed to a separator (7), and split to purified $\epsilon$-caprolactam (7a) and a mother liquid (7b),
   g) the mother liquid (7b) is recycled to the crystallizer (6).

6. Process according to claim 5, wherein a part of the mother liquid (7b) is purged and the purge is recycled to the distillation column (3) or to the distillation column (4).

7. Process according to claim 5, wherein the separator (7) is a crystal wash column.

8. Process according to claim 7, wherein the crystal wash column is a hydraulic wash column in which the purified $\epsilon$-caprolactam crystals are removed from the crystal bed, subsequently molten by a heat exchanger and a part of the molten $\epsilon$-caprolactam is recycled to the washcolumn as washing liquid.

9. Process according to claim 1, wherein, polycaprolactam processing waste, polycaprolactam carpet wast and/or polycaprolactam extraction wash water is treated in the cyclisation reactor.

* * * * *